(12) United States Patent
Sykes et al.

(10) Patent No.: US 10,124,091 B2
(45) Date of Patent: Nov. 13, 2018

(54) RADIOACTIVE MONOLAYER SURFACE COATING

(71) Applicant: Trustees of Tufts College, Boston, MA (US)

(72) Inventors: Charles Sykes, Somerville, MA (US); Alex Pronschinske, Arlington, MA (US); Colin Murphy, Somerville, MA (US)

(73) Assignee: Trustees of Tufts College, Medford, MA (US)

(*) Notice: Subject to any disclaimer, the term of this patent is extended or adjusted under 35 U.S.C. 154(b) by 0 days.

(21) Appl. No.: 15/311,215

(22) PCT Filed: May 15, 2015

(86) PCT No.: PCT/US2015/031037
§ 371 (c)(1),
(2) Date: Nov. 15, 2016

(87) PCT Pub. No.: WO2015/175914
PCT Pub. Date: Nov. 19, 2015

(65) Prior Publication Data
US 2017/0087279 A1    Mar. 30, 2017

Related U.S. Application Data

(60) Provisional application No. 62/081,096, filed on Nov. 18, 2014, provisional application No. 61/994,549, filed on May 16, 2014.

(51) Int. Cl.
*A61K 9/00* (2006.01)
*A61L 31/08* (2006.01)
(Continued)

(52) U.S. Cl.
CPC ........... *A61L 31/088* (2013.01); *A61L 27/303* (2013.01); *A61L 27/306* (2013.01); *A61L 27/54* (2013.01);
(Continued)

(58) Field of Classification Search
CPC .................................................. A61K 31/088
See application file for complete search history.

(56) References Cited

U.S. PATENT DOCUMENTS

| 6,461,433 B1 | 10/2002 | Carden, Jr. et al. |
| 2011/0014572 A1* | 1/2011 | Lal ............................ G03F 1/20 430/296 |

(Continued)

FOREIGN PATENT DOCUMENTS

WO    WO-2012/109157 A2    8/2012

OTHER PUBLICATIONS

International Search Report dated Aug. 18, 2015, from PCT/US15/31037.

*Primary Examiner* — Paul W Dickinson
(74) *Attorney, Agent, or Firm* — Foley Hoag LLP

(57) ABSTRACT

Disclosed are compositions including a film enriched with a radioisotope relative to its natural abundance, wherein the film has a thickness of one to ten atomic or molecular layers, decay of the radioisotope comprises emission of electrons, and a majority of the emitted electrons have an energy less than or equal to 700 electron volts (ev). Also disclosed are methods for making the compositions. The compositions can be used in microarrays, nanoarrays, microparticles, nanoparticles, power sources, sensing devices, and medical devices; they may also be used in a method of delivering low-energy electrons to a liquid, solid, molecular layer, or cell.

26 Claims, 8 Drawing Sheets

(51) Int. Cl.
*A61N 5/10* (2006.01)
*A61L 27/30* (2006.01)
*A61L 27/54* (2006.01)
*A61L 31/16* (2006.01)
*A61L 31/18* (2006.01)
*A61L 31/02* (2006.01)

(52) U.S. Cl.
CPC ............ *A61L 31/028* (2013.01); *A61L 31/084* (2013.01); *A61L 31/16* (2013.01); *A61L 31/18* (2013.01); *A61N 5/1001* (2013.01); *A61L 2300/44* (2013.01); *A61L 2400/12* (2013.01); *A61N 2005/1089* (2013.01)

(56) References Cited

U.S. PATENT DOCUMENTS

| | | | |
|---|---|---|---|
| 2013/0195979 A1 | 8/2013 | Tersigni | |
| 2015/0133568 A1* | 5/2015 | Zhao | C23C 18/1204 516/32 |

* cited by examiner (PRIOR ART)

RADIOACTIVE MONOLAYER SURFACE COATING

RELATED APPLICATIONS

This application is a § 371 national stage application based on Patent Cooperation Treaty Application serial number PCT/US2015/031037, filed May 15, 2015, which claims the benefit of priority to U.S. Provisional Patent Application No. 61/994,549, filed May 16, 2014; and U.S. Provisional Patent Application No. 62/081,096, filed Nov. 18, 2014.

GOVERNMENT SUPPORT

This invention was made with government support under Grant Nos. CHE-0844343 and CHE-1412402 awarded by the National Science Foundation. The government has certain rights in the invention.

BACKGROUND OF THE INVENTION

The interaction of high-energy radiation (gamma rays, X-rays, and beta particles) with matter produces not only primary impact damage, but also large numbers of non-thermal secondary electrons (~$10^4$ electrons per MeV of decay energy deposited). These lower energy electrons are the main drivers of radiation-induced chemical reactions as well as biological and materials damage, making them arguably the most important species in radiation chemistry. FIG. 1 shows that the majority of the secondary electrons have an energy less than 10 eV. Arumainayagam C R et al. (2010) *Surface Science Reports* 65:1-44. The dissociative mechanism at energies less than 10 eV is primarily from dissociative electron attachment, in which a short-lived negative ion of the molecule is formed and then dissociates into a radical fragment and an ion fragment. At higher energies electron impact excitation (>6 eV) and ionization (>10 eV) events occur. As is evident from FIG. 1, the plentiful low energy electrons produced from a high energy radioactive decay drive the majority of the chemistry/damage observed at the macro scale.

While macroscopic radioactive decay effects are well understood and have been utilized for decades, single-atom radiochemistry is almost completely unexplored. Nanoscale assembly and atomic-scale imaging of radioactive elements has not been attempted. Verkhoturov et al. observed that the Auger cascade from the electron capture (EC) decay of $^{55}$Fe supported on an alkylthiol and fluorocarbon monolayer was the main driver of molecular fragmentation and free ion production. Verkhoturov S V et al. (2001) *Phys Rev Lett* 87(3):037601.

Huang L et al. (1997) *J Chem Phys* 107(2):585-91 describes nonradioactive iodine adlayer structures on gold ($^{111}$Au) films on quartz, as studied using scanning tunneling microscopy (STM).

U.S. Patent Application Publication No. 2013/0302243 (incorporated herein by reference) to Borbély et al. discloses targeted, self-assembled nanoparticles radiolabeled with technetium-99m ($^{99m}$Tc).

SUMMARY OF THE INVENTION

Provided are radioactive coatings and films useful in the manufacture of shaped nano-scale low-energy electron emitters, including, without limitation, any of a variety of microarrays, nanoarrays, microparticles, nanoparticles, nanodevices, power sources, sensing devices, and medical devices. These 2-D radioactive coatings and films offer a platform for understanding the microscopic details of electron-induced processes and provide a route to nano-scale electron emitters.

$^{125}$I is commonly used in medical imaging, radiation therapy, and biological assays. The $^{125}$I-Au sample preparation methods described here are highly compatible with Au nanoparticles. Huang, L. et al. (1997) *J Chem Phys* 107: 585. Thus, in certain embodiments, this interface enhancement of biologically active low energy electrons can be used to offer nano-scale specificity for highly targeted nanoparticle therapies. Balagurumoorthy, P. et al. (2012) *Int J Radiat Biol* 88: 998-1008; McLaughlin, M. F. et al. (2013) *PLoS One* 8: e54531; Kim, Y.-H. et al. (2011) *Small* 7: 2052-60.

An aspect of the invention is a composition, comprising: a substrate; and a film enriched with a radioisotope relative to the natural abundance of said radioisotope; wherein said substrate comprises a first surface; the first surface is in contact with the film; the film has a thickness of one to ten atomic or molecular layers; decay of the radioisotope comprises emission of electrons; and a majority of the emitted electrons have an energy less than or equal to 700 electron volts (eV).

An aspect of the invention is a method of making said composition, comprising contacting a source of the radioisotope with the first surface of the substrate, wherein the source of the radioisotope is enriched with the radioisotope relative to the natural abundance of said radioisotope, thereby forming the film.

An aspect of the invention is a composition, comprising: a substrate; a film enriched with a radioisotope relative to the natural abundance of said radioisotope; and an intervening layer; wherein said substrate comprises a first surface; said intervening layer is positioned between the substrate and the film; the intervening layer comprises an inner surface and an outer surface; said first surface is in contact with said inner surface; said outer surface is in contact with said film; the film has a thickness of one to ten atomic or molecular layers; decay of the radioisotope comprises emission of electrons; and a majority of the emitted electrons have an energy less than or equal to 700 electron volts (eV).

An aspect of the invention is a method of making said composition, comprising contacting a source of the radioisotope with the outer surface of the intervening layer, wherein the source of the radioisotope is enriched with the radioisotope relative to the natural abundance of said radioisotope, thereby forming the film.

An aspect of the invention is a microarray or nanoarray, comprising a composition of the invention, wherein the film is patterned.

An aspect of the invention is a power source, comprising the composition of the invention.

An aspect of the invention is a sensing device, comprising the composition of the invention.

An aspect of the invention is a medical device, comprising the composition of the invention. In an embodiment, the medical device is an implantable medical device.

An aspect of the invention is a method of delivering low-energy electrons to a liquid, solid, molecular layer, or cell, comprising contacting a liquid, solid, molecular layer, or cell with the composition of the invention.

DETAILED DESCRIPTION OF THE INVENTION

Nuclear decay is one of the most extreme non-equilibrium effects and is central to energy related technologies. While macroscopic radioactive decay effects are well understood and have been utilized for decades, nanoscale effects of radioactive decay have barely been explored. A microscopic picture of how radioactive atoms can be assembled on surfaces/nanoparticles, how they decay, and how the resulting radiation affects their local molecular environment will provide fundamental knowledge about both materials and biological damage, uncover new non-equilibrium chemistries, fuel the discovery of methods for constructing nanoscale radioactive materials, and enable new technologies.

Figure 1:
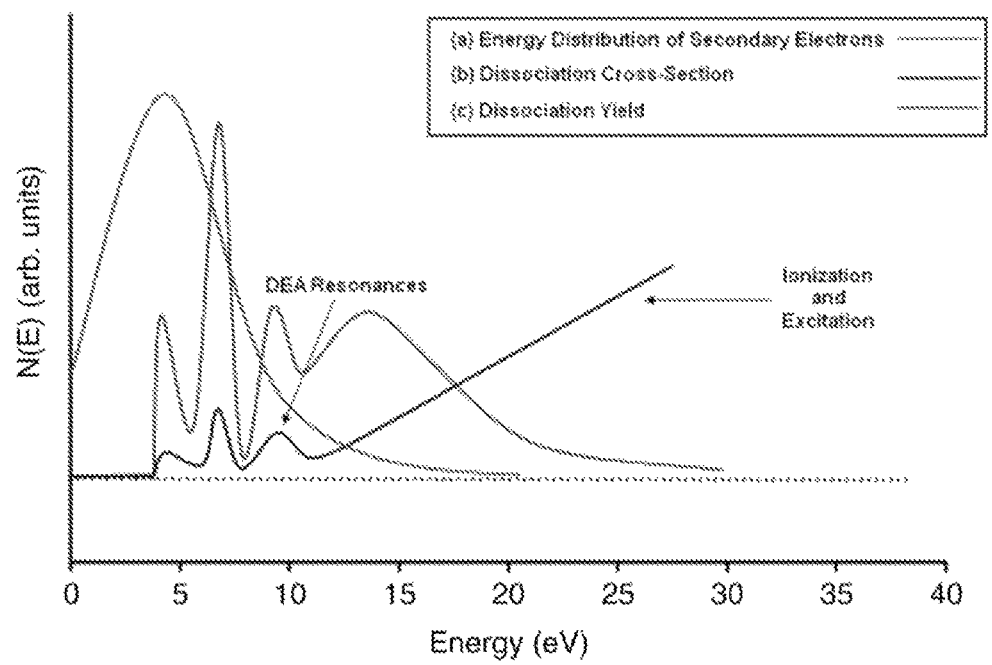
FIG. 1 is a graph from the prior art which depicts schematically (a) radiation-induced secondary electron energy distribution, (b) dissociation cross-section, and (c) dissociation yield. The majority of secondary electrons have energies below 10 eV.

The interaction of high-energy radiation (gamma rays, X-rays, and beta particles) with matter produces not only primary impact damage, but also large numbers of non-thermal secondary electrons (~10$^4$ electrons per MeV of decay energy deposited). These lower energy electrons are the main drivers of radiation-induced chemical reactions as well as biological and materials damage, making them arguably the most important species in radiation chemistry. FIG. 1 shows that nearly all of the secondary electrons have less than 10 eV of energy. The dissociative mechanism at energies less than 10 eV is primarily from dissociative electron attachment, in which a short-lived negative ion of the molecule is formed and then dissociates into a radical fragment and an ion fragment. At higher energies electron impact excitation (>6 eV) and ionization (>10 eV) events occur. In order to engineer chemical processes that harness the energy of nuclear radiation we must recognize that the creation of secondary electrons drives the majority of the resulting chemistry and therefore an understanding of how to control the creation, scattering and dosing of secondary electrons is paramount to advancing the utility and breadth of radiochemical processes.

While macroscopic radioactive decay effects are well understood, single atom radiochemistry is completely unexplored. Synthesis of well-defined monolayer films of radionuclides will enable imaging of radioactive elements and the ability to study decay events at the single atom level in real time. Scanning probes will allow us to observe the nuclear transmutation and, most importantly, understand how the resulting radiation affects the surrounding atoms/molecules; this will demonstrate the feasibility of our 2-D/nanoscale approach. Practically, the ability to assemble, functionalize, and pattern these 2-D layers of radioactive elements or radiolabeled molecules at the nanometer scale will open up many new possibilities for miniaturized power sources and novel tracking and sensing devices, and it will provide insight into the local effect of the secondary electrons that accompany high energy nuclear decay events.

Our approach opens up the possibility to engineer novel 2-D layers, films, coatings and arrays for tracking and sensing, and will enable a new platform to probe local effects in radioactive decay. Creating 2-D nanopatterned arrays of radionuclides will allow for new imaging and analysis techniques to be developed for quality control in fluid flows and in the production of films. These novel radionuclide surface chemistry procedures will be broadly applicable to metal nanoparticles enabling synthesis of new radioactive nanomaterials, such as radiolabeled ferromagnetic nanoparticles that would allow for in-situ manipulation, extraction, and reuse using external magnetic fields.

Further, iodine 125 (a/k/a $^{125}$I) is currently used to treat brain, prostrate and other cancers. By adsorbing iodine 125 on gold or other metal nanoparticles, its electron emission will be enhanced. The adsorption is achieved by adding a solution of iodine 125 to a solution of nanoparticles. Iodine binds strongly to gold and other metals. In addition to iodine, the nanoparticles would bind to tumor targeting species like antibodies, nuclear localization peptide sequences etc. that target cancer cells. This characteristic would also enable the nanoparticles to enter the nucleus of a cell, and irradiate its DNA directly. This process will work for any radioisotope of iodine, not just iodine 125, so species with different half-lives can be used. It will also work for S or P radionuclides etc.

An aspect of the invention is a composition, comprising: a substrate; and a film enriched with a radioisotope relative to the natural abundance of said radioisotope; wherein said substrate comprises a first surface; the first surface is in contact with the film; the film has a thickness of one to ten atomic or molecular layers; decay of the radioisotope comprises emission of electrons; and a majority of the emitted electrons have an energy less than or equal to 700 electron volts (eV).

As used herein, a "substrate" refers to any solid phase material or substance. The substrate can be uniform (homogeneous) or nonuniform (inhomogeneous) in composition. In an embodiment, a substrate is a solid. In an embodiment, a substrate is essentially fixed in shape and dimensions. In another embodiment, a substrate is flexible, e.g., a film. In another embodiment, a substrate is deformable. In another embodiment, a substrate is a particle, nanoparticle, microparticle, nanosphere, or microsphere. In certain embodiments, the substrate is a nanoparticle.

As used herein, a "film" refers to a thin, conformable layer of material. In an embodiment, the film can be applied to or otherwise placed in contact with a substrate. In an embodiment, the film is adhered to or adherent to a substrate. In an embodiment, the film is coated on the substrate (e.g., covering some of or the entirety of the surface of a particle or sphere).

In an embodiment, the film is a monolayer. As used herein, a "monolayer" refers to a film having a thickness of essentially one atomic layer or one molecular layer. For example, in one embodiment a monolayer is essentially a 2-D array of atoms; the atoms can be homogeneous or heterogeneous. As another example, in one embodiment a monolayer is essentially a 2-D array of molecules; the molecules can be homogeneous or heterogeneous.

In other embodiments, the film is 2, 3, 4, 5, 6, 7, 8, 9, or 10 atomic or molecular layers thick. In some embodiments, the film can have a range of thicknesses, for example, from one to ten atomic or molecular layers. In some embodiments, the film can have a gradient of thickness, for example, from one to ten atomic or molecular layers.

The film is enriched with a radioisotope relative to the natural abundance of said radioisotope. As used herein, a radioisotope is enriched relative to the natural abundance of said radioisotope when the radioisotope is present in an amount or concentration at least 5 percent greater than the natural abundance. For example, the natural abundance of $^{125}$I is effectively zero. $^{125}$I is said to be enriched when it is present in an amount or concentration of at least 5 percent. Isotope abundances are available from IUPAC Commission on Isotopic Abundances and Atomic Weights.

In an embodiment in accordance with any one of the foregoing, the radioisotope is selected from the group consisting of electron capture radioisotopes, negative beta emitters, and positive beta emitters.

In an embodiment in accordance with any one of the foregoing, the radioisotope is an electron capture radioisotope.

In an embodiment in accordance with any one of the foregoing, the radioisotope is selected from the group consisting of $^{3}$H, $^{11}$C, $^{18}$F, $^{32}$P, $^{33}$P, $^{35}$S, $^{51}$Cr, $^{55}$Fe, $^{56}$Co, $^{57}$Co, $^{125}$I, and $^{131}$I.

In an embodiment in accordance with any one of the foregoing, the radioisotope is $^{125}$I.

In an embodiment in accordance with any one of the foregoing, the substrate is mica.

In an embodiment in accordance with any one of the foregoing, the first surface comprises gold, silver, or silicon.

In an embodiment in accordance with any one of the foregoing, the first surface comprises gold.

In an embodiment in accordance with any one of the foregoing, the first surface is gold.

In an embodiment in accordance with any one of the foregoing, the first surface comprises graphite (e.g., highly ordered pyrolytic graphite (HOPG)) or graphene.

In an embodiment in accordance with any one of the foregoing, the first surface is graphite (e.g., highly ordered pyrolytic graphite (HOPG)) or graphene.

In an embodiment in accordance with any one of the foregoing, the first surface is HOPG.

In an embodiment in accordance with any one of the foregoing, the first surface is graphene.

An aspect of the invention is a method of making the foregoing composition, comprising contacting a source of the radioisotope with the first surface of the substrate, wherein the source of the radioisotope is enriched with the radioisotope relative to the natural abundance of said radioisotope, thereby forming the film.

In an embodiment in accordance with the foregoing method, the contacting is drop depositing.

In an embodiment in accordance with the foregoing method, the contacting is solution depositing.

In an embodiment in accordance with the foregoing method, the contacting is vapor depositing.

In an embodiment in accordance with any one of the foregoing, the film is a monolayer.

In an embodiment in accordance with any one of the foregoing, the radioisotope is selected from the group consisting of electron capture radioisotopes, negative beta emitters, and positive beta emitters.

In an embodiment in accordance with any one of the foregoing, the radioisotope is an electron capture radioisotope.

In an embodiment in accordance with any one of the foregoing, the radioisotope is selected from the group consisting of $^{3}$H, $^{11}$C, $^{18}$F, $^{32}$P, $^{33}$P, $^{35}$S, $^{51}$Cr, $^{55}$Fe, $^{56}$Co, $^{57}$Co, $^{125}$I, and $^{131}$I.

In an embodiment in accordance with any one of the foregoing, the radioisotope is $^{125}$I.

In an embodiment in accordance with any one of the foregoing, the substrate is mica.

In an embodiment in accordance with any one of the foregoing, the substrate is graphite (e.g., highly ordered pyrolytic graphite (HOPG)) or graphene.

In an embodiment in accordance with any one of the foregoing, the substrate is HOPG.

In an embodiment in accordance with any one of the foregoing, the substrate is graphene.

In an embodiment in accordance with any one of the foregoing, the first surface is graphite (e.g., highly ordered pyrolytic graphite (HOPG)) or graphene.

In an embodiment in accordance with any one of the foregoing, the first surface is HOPG.

In an embodiment in accordance with any one of the foregoing, the first surface is graphene.

In an embodiment in accordance with any one of the foregoing, the first surface comprises gold, silver, or silicon.

In an embodiment in accordance with any one of the foregoing, the first surface comprises gold.

In an embodiment in accordance with any one of the foregoing, the first surface is gold, silver, or silicon.

In an embodiment in accordance with any one of the foregoing, the first surface is gold.

An aspect of the invention is a composition, comprising: a substrate; a film enriched with a radioisotope relative to the natural abundance of said radioisotope; and an intervening layer; wherein said substrate comprises a first surface; said intervening layer is positioned between the substrate and the film; the intervening layer comprises an inner surface and an outer surface; said first surface is in contact with said inner surface; said outer surface is in contact with said film; the film has a thickness of one to ten atomic or molecular layers; decay of the radioisotope comprises emission of electrons; and a majority of the emitted electrons have an energy less than or equal to 700 electron volts (eV).

In an embodiment in accordance with the foregoing, the film is a monolayer.

In an embodiment in accordance with any one of the foregoing, the radioisotope is selected from the group consisting of electron capture radioisotopes, negative beta emitters, and positive beta emitters.

In an embodiment in accordance with any one of the foregoing, the radioisotope is an electron capture radioisotope.

In an embodiment in accordance with any one of the foregoing, the radioisotope is selected from the group consisting of $^3$H, $^{11}$C, $^{18}$F, $^{32}$P, $^{33}$P, $^{35}$S, $^{51}$Cr, $^{55}$Fe, $^{56}$Co, $^{57}$Co, $^{125}$I, and $^{131}$I.

In an embodiment in accordance with any one of the foregoing, the radioisotope is $^{125}$I.

In an embodiment in accordance with any one of the foregoing, the substrate is mica.

In an embodiment in accordance with any one of the foregoing, the first surface comprises gold, silver, or silicon.

In an embodiment in accordance with any one of the foregoing, the first surface comprises gold.

In an embodiment in accordance with any one of the foregoing, the first surface is gold, silver, or silicon.

In an embodiment in accordance with any one of the foregoing, the first surface is gold.

In an embodiment in accordance with any one of the foregoing, the outer surface is graphite (e.g., highly ordered pyrolytic graphite (HOPG)) or graphene.

In an embodiment in accordance with any one of the foregoing, the outer surface is HOPG.

In an embodiment in accordance with any one of the foregoing, the outer surface is graphene.

In an embodiment in accordance with any one of the foregoing, the intervening layer comprises gold, silver, or silicon.

In an embodiment in accordance with any one of the foregoing, the outer surface comprises gold, silver, or silicon.

In an embodiment in accordance with any one of the foregoing, the outer surface comprises gold.

In an embodiment in accordance with any one of the foregoing, the outer surface is gold, silver, or silicon.

In an embodiment in accordance with any one of the foregoing, the outer surface is gold.

In an embodiment in accordance with any one of the foregoing, the intervening layer comprises graphite (e.g., highly ordered pyrolytic graphite (HOPG)) or graphene.

In an embodiment in accordance with any one of the foregoing, the intervening layer comprises HOPG.

In an embodiment in accordance with any one of the foregoing, the intervening layer comprises graphite or graphene.

In an embodiment in accordance with any one of the foregoing, the intervening layer is graphite (e.g., highly ordered pyrolytic graphite (HOPG)) or graphene.

In an embodiment in accordance with any one of the foregoing, the intervening layer is HOPG.

In an embodiment in accordance with any one of the foregoing, the intervening layer is graphite or graphene.

An aspect of the invention is a method of making the foregoing composition, comprising contacting a source of the radioisotope with the outer surface of the intervening layer, wherein the source of the radioisotope is enriched with the radioisotope relative to the natural abundance of said radioisotope, thereby forming the film.

In an embodiment in accordance with the foregoing method, the contacting is drop depositing.

In an embodiment in accordance with the foregoing method, the contacting is solution depositing.

In an embodiment in accordance with the foregoing method, the contacting is vapor depositing.

In an embodiment in accordance with any one of the foregoing, the film is a monolayer.

In an embodiment in accordance with any one of the foregoing, the radioisotope is selected from the group consisting of electron capture radioisotopes, negative beta emitters, and positive beta emitters.

In an embodiment in accordance with any one of the foregoing, the radioisotope is an electron capture radioisotope.

In an embodiment in accordance with any one of the foregoing, the radioisotope is selected from the group consisting of $^3$H, $^{11}$C, $^{18}$F, $^{32}$P, $^{33}$P, $^{35}$S, $^{51}$Cr, $^{55}$Fe, $^{56}$Co, $^{57}$Co, $^{125}$I, and $^{131}$I.

In an embodiment in accordance with any one of the foregoing, the radioisotope is $^{125}$I.

In an embodiment in accordance with any one of the foregoing, the substrate is mica.

In an embodiment in accordance with any one of the foregoing, the substrate is graphite (e.g., highly ordered pyrolytic graphite (HOPG)) or graphene.

In an embodiment in accordance with any one of the foregoing, the substrate is HOPG.

In an embodiment in accordance with any one of the foregoing, the substrate is graphene.

In an embodiment in accordance with any one of the foregoing, the first surface is graphite (e.g., highly ordered pyrolytic graphite (HOPG)) or graphene.

In an embodiment in accordance with any one of the foregoing, the first surface is HOPG.

In an embodiment in accordance with any one of the foregoing, the first surface is graphene.

In an embodiment in accordance with any one of the foregoing, the first surface comprises gold, silver, or silicon.

In an embodiment in accordance with any one of the foregoing, the first surface comprises gold.

In an embodiment in accordance with any one of the foregoing, the first surface is gold, silver, or silicon.

In an embodiment in accordance with any one of the foregoing, the first surface is gold.

In an embodiment in accordance with any one of the foregoing, the intervening layer comprises gold, silver, or silicon.

In an embodiment in accordance with any one of the foregoing, the intervening layer comprises gold.

In an embodiment in accordance with any one of the foregoing, the intervening layer is gold, silver, or silicon.

In an embodiment in accordance with any one of the foregoing, the intervening layer is gold.

In an embodiment in accordance with any one of the foregoing, the intervening layer comprises graphite (e.g., highly ordered pyrolytic graphite (HOPG)) or graphene.

In an embodiment in accordance with any one of the foregoing, the intervening layer comprises HOPG.

In an embodiment in accordance with any one of the foregoing, the intervening layer comprises graphene.

In an embodiment in accordance with any one of the foregoing, the intervening layer is graphite (e.g., highly ordered pyrolytic graphite (HOPG)) or graphene.

In an embodiment in accordance with any one of the foregoing, the intervening layer is HOPG.

In an embodiment in accordance with any one of the foregoing, the intervening layer is graphene.

An aspect of the invention is a microarray or nanoarray, comprising a composition of the invention, wherein the film is patterned.

An aspect of the invention is a power source, comprising the composition of the invention.

An aspect of the invention is a sensing device, comprising the composition of the invention.

An aspect of the invention is a medical device, comprising the composition of the invention. In an embodiment, the medical device is an implantable medical device.

An aspect of the invention is a method of delivering low-energy electrons to a liquid, solid, molecular layer, or cell, comprising contacting a liquid, solid, molecular layer, or cell with the composition of the invention.

In accordance with each of the compositions and methods above, in an embodiment, the first surface is substantially planar.

In accordance with each of the compositions and methods above, in an embodiment, the first surface is substantially non-planar. For example, the first surface can be textured, e.g., corrugated. As another example, the first surface can take the form of the surface of a sphere or a portion thereof.

In accordance with each of the compositions and methods above, in an embodiment, the substrate is a nanoparticle.

In accordance with each of the compositions and methods above, in an embodiment, the nanoparticle is a ferromagnetic nanoparticle.

In accordance with each of the compositions and methods above, in an embodiment, the substrate is a microparticle.

In accordance with each of the compositions and methods above, in an embodiment, the nanoparticle is a ferromagnetic microparticle.

An aspect of the invention is a microarray or nanoarray, comprising a composition of the invention, wherein the film is patterned.

An aspect of the invention is a power source, comprising the composition of the invention.

An aspect of the invention is a sensing device, comprising the composition of the invention.

An aspect of the invention is a medical device, comprising the composition of the invention. In an embodiment, the medical device is an implantable medical device.

An aspect of the invention is a method of delivering low-energy electrons to a liquid, solid, molecular layer, or cell, comprising contacting a liquid, solid, molecular layer, or cell with the composition of the invention.

Our first experiments will focus on constructing and understanding pure and diluted radionuclide films on commercially-available substrates (Au/mica, HOPG) as well as on a variety of nanoparticles. By carefully designing the molecules that contain the radionuclides we will be able to produce a range of simple, robust, and air-stable systems that can be prepared quickly and easily in ambient conditions. To accomplish this we will use radionuclides including $^{35}$S and $^{3}$H incorporated into alkanethiol SAMs, $^{32}$P and $^{33}$P in the form of trimethylphosphine (PMe$_3$) monolayers, $^{51}$Cr in large aromatic molecules, and $^{3}$H incorporated into fatty acids (see Table 1). For example, alkanethiol SAMs have been of great interest for roughly the last 30 years, and their utility in many fields, such as sensing, device assembly, molecular electronics, and microelectromechanical systems, has been thoroughly demonstrated, making them a great platform for studying nanoscale radiochemistry. Furthermore, metal elements that undergo electron capture (e.g., $^{51}$Cr, $^{55}$Fe, and $^{57}$Co) have been of studied due to their emission of Auger electrons and their high potential stability with respect to decay when incorporated in inorganic compounds. Nath, A et al. (2001) *J Radioanalytical Nuclear Chem* 247:589-91; Verkhoturov, S et al. (2001) *Phys Rev Letts* 87:037601. The simplicity of these systems and abundance of established experimental procedures will both accelerate our start in this novel venture and offer the first portable, atomically well-defined, 2-D radioactive samples.

TABLE 1

Summary of nuclear decay information for radioisotopes of interest. The isotopes listed undergo either beta decay (β$^-$) or electron capture (EC), which will have different radiation yield profiles. The decay energy reflects the energy difference between the parent and daughter nuclei and is related to the energy of the primary radiation; the wide range of energies will result in varying amounts of reactive secondary electrons produced by scattering in the support substrate.

| Radio-isotope | Half-life | Decay mode | Daughter isotope | Decay Energy |
|---|---|---|---|---|
| $^3$H | 12.32 years | β$^-$ | $^3$He | 18.6 keV |
| $^{32}$P | 14.26 days | β$^-$ | $^{32}$S | 1.710 MeV |
| $^{33}$P | 25.34 days | β$^-$ | $^{33}$S | 249 keV |
| $^{35}$S | 87.32 days | β$^-$ | $^{35}$Cl | 167 keV |
| $^{51}$Cr | 27.70 days | EC | $^{51}$V | 753 keV |
| $^{55}$Fe | 2.737 years | EC | $^{55}$Mn | 231 keV |
| $^{57}$Co | 271.7 days | EC | $^{57}$Fe | 836 keV |
| $^{125}$I | 59.4 days | EC | $^{125}$Te | 186 keV |

Phosphorous has two common radioactive isotopes, both of which decay via β$^-$-decay: $^{32}$P and $^{33}$P. In this system the daughter atom ($^{32}$S or $^{33}$S) would have a significant amount of recoil energy, which could potentially dissociate its bonds. Given that the phosphorus in PPh$_3$ and PMe$_3$ would decay into sulfur, one would also expect a dramatic restructuring of the molecule itself in response to the change in valency of the element. We minimally expect that a methyl group would be released to satisfy the valency of the newly formed sulfur atom. The chemistry is complicated by the recoil energy of the daughter nucleus which can break otherwise stable bonds and will vary different amounts for different isotopes (e.g., the mean recoil energy from $^{32}$P decay is 20 times higher than that of $^{33}$P). In the same manner, we will investigate the β-decay of $^{35}$S incorporated in alkanethiols on Au(111) into $^{35}$Cl. Enriched alkanethiols would present similar bond stability and daughter valency issue as $^{32}$P/$^{33}$P but with a valency shift from 2 to 1 ($C_nH_{2n+1}{}^{35}$S/Au→$C_nH_{2n+1}{}^{35}$Cl$^+$/Au). In the case of enriched alkanethiol decay the non-equilibrium state can be resolved in one of two ways. Either the $^{35}$Cl stays attached to the molecule and becomes physisorbed to the substrate or desorbed, or an alkyl radical would desorb, leaving the $^{35}$Cl atom chemisorbed to the surface. The use of various radioisotopes in this manner will allow us to expand the chemical scope of our investigation and give it direct applicability to the existing applications of alkanethiol SAMs. These systems also offer the intriguing prospect of observing the before and after effect a nuclear decay event triggering a chemical bonding change in a single molecule. In this way we will create platforms that will provide a new microscopic understanding of radiation chemistry, biological degradation, and material damage.

Sykes has examined the behavior of non-radioactive PMe$_3$ and PPh$_3$ on Au(111) after a variety of annealing treatments using STM. Jewell, A D et al. (2012) *Chemistry (Weinheim an der Bergstrasse, Germany)* 18:7169-78; Jewell, A D et al. (2010) *Phys. Rev. B* 82:205401. Our UHV experimental approach offers a relatively straightforward, accurate, and highly reproducible sample preparation method, leading to a better understanding of the monolayer structures. Our results reveal the complex self-assembly behavior of PMe$_3$ and PPh$_3$, common ligands in organic, organometallic, and metal nanoparticle synthesis. In contrast to other popular capping agents such as thiols, the surface chemistry of this important species has to date gone almost completely unexamined.

In order to understand secondary electron reactions at surfaces the nuclear decay secondary electron cascades will be simulate using the STM tip as an electron source. It has been shown by multiple groups that controlled electron injection into surface-bound molecules above specific energy thresholds (STM tip voltages) can produce similar effects similar to what we may see during dissociative decay events, including diffusion, bond formation/cleavage, and desorption of surface species. The P—Au bond, for example, is weak covalent/dative in nature, and so should be susceptible to undergoing dissociative electron attachment, electron impact fragmentation, or dissociation leading to desorption mediated by Au—P vibrational excitation. In STM the threshold energy for these events can be determined by controlled injection of tunneling electrons with atomic precision. Using this approach we will be able to replicate Sykes's observed radiation damage with electrons of specific energy and hence begin to understand what flux and energy of electrons lead to various types of radiation damage.

In these proposed 2-D systems a multitude of lower energy electrons will be produced at the surface of the films and nanoparticles due to inelastic backscattering of the inward emitted electrons. Therefore, the decay of surface-bound radionuclides is likely to produce chemically significant radiation, allowing us to study and harness the effects of both primary ionizing radiation (from internal conversion) but most significantly the secondary ionizing radiation (from Auger electrons and backscattering). Our imaging experiments will reveal the extent of local and long range damage caused by the radioactive decay as well as allow us to count events and relate these single atom statistics to ensemble half-life and more importantly the resulting damage. These will enable a new microscopic understanding of radiation chemistry, biological degradation, and material damage at the atomic level.

Our radioactivity work will be extended to the synthesis and characterization of well-defined materials that emit controlled amounts of radiation, primarily in the form of electrons of about 5 eV. This will open up possibilities to engineer novel materials for tracking and sensing and will enable a new platform to probe local effects in radioactive decay and non-equilibrium chemistry. Given that the secondary electrons are produced in the metal films/nanoparticles via scattering of the primary radiation, the thickness of the metal films or diameter of the nanoparticles will dictate the energy distribution of the emitted secondary electrons. Physical vapor deposition will be used to grow and characterize metal and oxide films with controllable thickness. This will allow the energy distribution and flux of the secondary electrons to be controlled. By comparing 2-D films to "0-D" nanoparticles of various sizes and materials, we will gain a fuller understanding of the conversion of nuclear decay energy into chemically important secondary electrons of about 5 eV (FIG. 1). We will synthesize or purchase metal nanoparticles of a range of sizes from 2 to >100 nm in size. For example, Au, Pt, and Ag nanoparticles of controlled size will be produced and capped with radionuclide-containing alkane thiols and phosphines, and radioactive isotopes of Iodine.

These novel radionuclide surface chemistry procedures will be broadly applicable to 0-D metal nanoparticles enabling synthesis of new radioactive nanomaterials, such as radiolabeled ferromagnetic nanoparticles that would allow for in-situ manipulation, extraction, and reuse using external magnetic fields. Surface-bound dye molecules (e.g., resorufin) reduced by the secondary electrons will allow us to image and monitor individual nanoparticles with single molecule luminescence so that many photons are detected for each chemical transformation event.

Practically, the ability to assemble, functionalize, and pattern 2-D layers and nanoparticles with radioactive elements or radiolabeled molecules at the nanometer scale, using the group's combined synthesis and measurement abilities, will enable a completely new approach to studying and driving non-equilibrium chemistry and open up many new possibilities for miniaturized power sources, novel tracking and sensing devices, radiation damage resistant materials, and will provide insight into the local effect of the secondary non-thermal electrons that accompany high energy nuclear decay events.

In certain embodiments, the radio isotopes are loaded onto the outside surface of metal nanoparticles or nanospheres that are then directed to tumor sites via either their natural buildup in vascular regions of the tumor or via targeting with antibodies or nuclear localization peptides. This will have two significant benefits over current therapies in that (1) the radio isotope is not encapsulated by metal which will allow full effect of the emitted electrons in terms of tumor destruction and (2) there will be significant amplification of the low energy (0-30 eV) electrons via secondary scattering in the metallic nanoparticle or nanosphere on which they are supported.

EXAMPLES

Having now described the present invention in detail, the same will be more clearly understood by reference to the following examples, which are included herewith for purposes of illustration only and are not intended to be limiting of the invention.

Example 1

Initial experiments focus on constructing and understanding pure and diluted $^{125}$I films on commercially-available Au/mica substrates, which affords a simple, robust, and air-stable system that can be prepared quickly and easily in ambient conditions. For brevity we focus our discussion of specific experimental goals on a set of $^{125}$I experiments; however, the same approaches and techniques for studying other radionuclides will allow us to expand and generalize our approach. Iodine forms chemisorbed monolayers on Au(111), which can be readily imaged via STM with atomic resolution under both ambient and ultra-high vacuum (UHV) conditions. Huang, L et al. (1997) *J Chem Phys* 107585-591; Haiss, W et al. (1992) *Surface Science* 274: L593-L598. The simplicity of this system and abundance of established experimental procedures will both accelerate our work and offer the first portable, atomically well-defined, 2-D radioactive samples. In terms of both preparation methods and film robustness, halide monolayers on metals are similar to the ubiquitous alkanethiol self-assembled monolayers (SAMs) on gold. Alkanethiol SAMs have been of great interest for the last 30 years, and their utility in many fields such as sensing (Malinsky, M D et al. (2001) *J Am Chem Soc* 123:1471-2; Wink, T et al. (1997) *Analyst* 122: 43R-50R), device assembly (Xiong, X et al. (2003) *J Microelectromechanical Systems* 12:117-27; Xia, Y et al. (1996) *Microelectronic Engineering* 32:255-68; Chandekar, A et al. (2006) *Langmuir* 22:8071-7; Ahn, H et al. (2003) *J Phys Chem B* 107:6565-72), molecular electronics (Sung, I-H et al. (2003) *Wear* 255:808-18; Gau, J-J et al. (2001) *Biosensors Bioelectronics* 16:745-55), and microelectromechanical systems (MEMS) have been demonstrated (Ge, Y et al. (2009) *J Phys Chem C* 113, 4575-83). Halide SAMs have also been studied for 30+ years for their passivating and anti-corrosion applications, and it is these properties that make $^{125}$I monolayers an ideal first system for us to transition the assembly, study, and use of radionuclides into 2-D and nanoscale environments. While we focus much of our initial efforts on $^{125}$I experiments and anticipated results, we plan to expand the study to other commonly used radionuclides including $^{35}$S and/or $^{3}$H incorporated into alkanethiol SAMs, $^{32}$P or $^{33}$P in the form of trimethylphosphine (PMe$_3$) monolayers, $^{51}$Cr in large aromatic molecules, and $^{3}$H incorporated into fatty acids assembled in films on graphite samples.

Iodine-125 ($^{125}$I) decays via electron capture (EC) with a half-life of 59.4 days, which is in the ideal range for our purposes. The decay occurs in two steps: EC with neutrino emission, followed by γ-emission or internal conversion. It should be noted that although kinetic recoil energy of the daughter atom can be significant with respect to cleaving it from chemical bonds to neighboring atoms for $^{125}$I the neutrino imparts a negligible 0.1 eV of recoil energy on the newly formed $^{125}$Te. Ertl, H et al. (1970) *Phys Med Biol* 15:447. During EC, an electron in either the K- or L-shell is combined with a proton in the nucleus to form a neutron and transmute the atom to an excited state of $^{125}$Te. The excited $^{125}$Te will stabilize 7% of the time by emitting a 35 keV γ-ray and 93% of the time by internal conversion (ejection of a core shell electron, which may be accompanied by X-ray radiation). The core holes of the daughter nuclide will subsequently be filled through the emission of soft X-rays and Auger electrons. On average 0.232 Auger electrons will be emitted per decay, with an energy of 500 eV or more. Ertl, H et al. (1970) *Phys Med Biol* 15:447. Lower energy electrons will also be produced due to inelastic backscattering of the inward-emitted electrons. Therefore, the decay of $^{125}$I atoms is likely to produce chemically significant radiation, allowing us to utilize both primary ionizing radiation (from internal conversion) and secondary ionizing radiation (from Auger electrons and backscattering).

Figure 2:
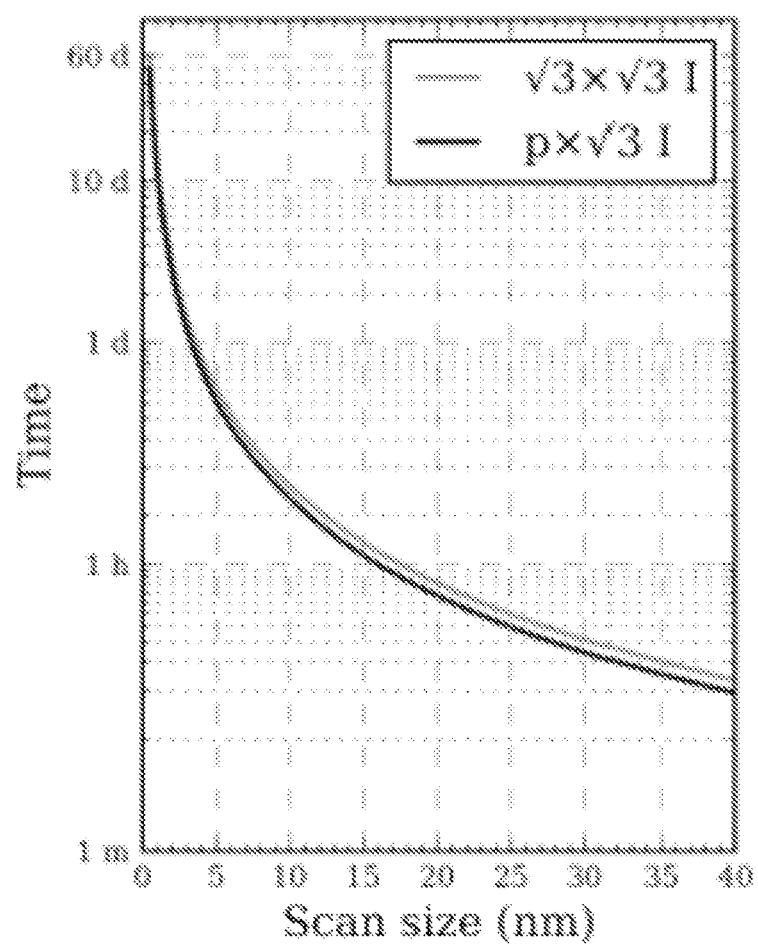
FIG. 2 is graph depicting the amount of time at which a square area of pure $^{125}$I assembled on Au(111) will have a 0.50 chance of still being pristine (i.e., median time to first atomic decay event) for various iodine coverage phases. The phases can be controlled via iodine solution concentration and deposition time. Scan size denotes the side length of a square scanning tunneling microscopy (STM) imaging area. Time is denoted on a logarithmic scale in units of minutes (m), hours (h), and days (d).

Given that we can control the number of atoms in our STM scan area and the ratio of $^{125}$I:$^{127}$I, we can in turn control the stochastic rate at which a single atomic decay will occur inside a defined imaging area of the iodine film. We have calculated the median time to the first atomic decay inside a pristine area for various STM scan sizes, which is shown in FIG. 2. The films will be made from fresh $^{125}$I solution shipped to the lab within 24 hours, after which less than 1% of the $^{125}$I will have decayed. Using the same tools and glassware, we will also make a "0%" enriched (i.e., non-radioactive) sample, so that we can use it as a control when quantifying the amount of film damage that arises from the decay events, as opposed to imperfections from the deposition process. Some samples will be made with an enrichment of 16% $^{125}$I so that, while minimizing the overall activity, within a single day of scanning we will have a statistical guarantee (>99.97%) of observing the decay of at least one $^{125}$I atom in a locally pristine 36×36 nm$^2$ area of the film with atomic resolution. Other samples will be made with 100% $^{125}$I and 1% $^{125}$I, allowing us to study the radiation effects on vastly different rate scales with both STM and X-ray photoelectron spectroscopy (XPS).

It has been shown that controlled electron injection into surface-bound molecules above specific energy thresholds (STM tip voltages) can produce similar effects similar to what we may see during dissociative decay events, including diffusion, bond formation/cleavage and desorption of surface species. The I—Au bond is covalent in nature and so should be susceptible to undergoing dissociative electron attachment, electron impact fragmentation, or dissociation leading to desorption mediated by Au—I vibrational excitation. In STM the threshold energy for these events can be determined by controlled injection of tunneling electrons with atomic precision. In this way we will be able to replicate the observed radiation damage with electrons of specific energy and hence begin to understand what flux and energy of electrons lead to various types of radiation damage.

Initial experiments will answer some very basic questions about how to construct novel 2-D radioactive films and how radiation damage by low energy secondary electrons is manifested at the nanoscale. We will then expand the scope of our nanoscale radiation research to other well-known systems that we can incorporate radioactive isotopes. Our group has already published research regarding the surface chemistry of PMe$_3$ on Au(111). Jewell, A D et al. (2010) *Phys Rev B* 82:205401. Phosphorous has two common radioactive isotopes, both of which decay via β$^-$-decay (n→p+e$^-$+$\bar{v}_e$): $^{32}$P and $^{33}$P. In this system the daughter atom ($^{32}$S or $^{33}$S) would have a significant amount of recoil energy, which could potentially dissociate its bonds. Given that the $^{32}$P or $^{33}$P in PMe$_3$ would decay into $^{32}$S or $^{33}$S, one would also expect a dramatic restructuring of the molecule itself in response to the change of element. We minimally expect that a methyl group would be ejected to satisfy the valency of the newly formed S atom.

In the same manner, we will investigate the β$^-$-decay of $^{35}$S incorporated in alkanethiols on Au(111) into $^{35}$Cl.

Enriched alkanethiols would present similar bond stability and daughter valency issue as $^{32}P/^{33}P$ but with an incremental change in absolute valency. This will allow us to expand the chemical scope of our investigation and give it direct applicability to the existing application of alkanethiol SAMs. These systems offer the intriguing prospect of observing the before and after effect a nuclear event triggering a chemical bonding change in a single molecule.

The emission of multiple Auger electrons during EC decay is a useful attribute of $^{125}I$. Studies have shown that I/Au(111) can serve as a substrate for much larger molecules, such as porphyrins and poly(3,4-ethylenedioxythiophene). In this manner $^{125}I$-coated surfaces will serve as well defined, robust, planar sources of ionizing radiation. This will allow us to study the effects of secondary electron damage in real-time to other chemical species. As the project advances we will incorporate metal radioisotopes into inorganic molecules. $^{51}Cr$ decays via EC and it is known that non-radioactive Cr can easily be incorporated into porphyrins to form chromium phthalocyanine (CrPc). By depositing CrPc molecules onto a metal surface in UHV we will be able to observe not only the secondary electron damage, but also the resiliency of the metal coordination bonds. After the decay of the $^{51}Cr$ into $^{51}V$ there will be a clear difference in both STM imaging and point spectroscopy between the original and VPc product molecules. It has been suggested that the π bonds of the phthalocyanine molecules should protect the molecule from the recoil energy of the decaying metal center and this system is an ideal test bed to probe these phenomena at the single molecule level.

Sample Preparation

The sample preparation method for the aforementioned films is well established, flexible, and somewhat forgiving. Previous studies have shown that an iodine film can be deposited onto the gold surface from solutions in air (Huang, L et al. (1997) *J Chem Phys* 107: 585-591; Haiss, W et al. (1992) *Surface Science* 274:L593-L598), from solution in an electrochemical cell (Bravo, B G et al. (1991) *J Phys Chem* 95: 5245-9; Lapitan L D S et al. (2012) *Electrochimica Acta* 62: 433-40), and by vapor deposition under vacuum (Cochran, S et al. (1980) *Surface Sci* 95: 359-66; Zheleva, Z V et al. (2010) *Phys Chem Chem Phys* 12: 10754-8). For our study we will deposit the $^{125}I$ from a solution of $^{125}I^-$ in ultra-pure $H_2O$ onto a clean $H_2$ flame-annealed Au/mica sample ($^{125}I$ solution obtained from PerkinElmer, Au/mica from Agilent Technologies). All of the steps in this deposition process are straightforward and reproducible, which will contribute to the success of the experiments. The simplicity of an ambient solution deposition procedure allows us to easily vary the enrichment of the film by diluting the $^{125}I$ solution with regular $^{127}I$. After the deposition has completed (3-12 min. of soaking) the sample will be cleaned by washing with 99.99% pure methanol, and is then ready for measurement. The uses of $^{35}S$, $^{32}P/^{33}P$, and $^{51}Cr$ as we have discussed have their own unique but well-established preparation procedures.

Mixing Deposition Solution

There are four deposition solutions that will be used for sample creation, referred to by their proportion of radioactive iodine: 100%, 30%, 10%, and 1%. The 100% solution will simply be the stock 350 mCi/mL Na$^{125}I$, $10^{-5}$ M NaOH solution ("PerkE$_{350}$"). The deposition solutions should be made in cleaned glassware.

30% $^{125}I$ solution: mix 10 μL of PerkE$_{350}$ and 15 μL of Stock I127 Solution 10% $^{125}I$ solution: mix 5 μL of PerkE$_{350}$ and 33 μL of Stock I127 Solution 1% $^{125}I$ solution: mix 5 μL of PerkE$_{350}$ and 380 μL of Stock I127 Solution

| Stock I127 Solution | | |
|---|---|---|
| Solution | $^{127}I$ Concentration | pH |
| NaI, NaOH in $H_2O$ | 0.161 mM | 9 |

Drop Depositing Iodine Monolayer

Step 1. Place a 7 microliter (μL) drop at the center of the gold sample surface. It is very important that the drop does not spread out. If the drop spreads out, immediately rinse it off with methanol, dry the sample, and re-attempt the dropping.

Step 2. Evaporate the drop using dry $N_2$ or He gas for the iodine to deposit on the gold surface.

Step 3. Rinse the surface residue off with methanol, and dry the surface.

Step 4. Repeat Steps 1-3 three times.

Step 5. Rinse the sample thoroughly with methanol (>99.9% pure). Using a clean Pasteur pipette, flush the surface with five full aliquots of methanol.

Instrumentation

Given that the as-formed radioactive films decay exponentially, we will use our entire fleet of STMs (2 ambient, 2 UHV) to image the time-sensitive samples. This parallel processing strategy will ensure that the decay events are monitored in both vacuum and ambient atmospheres, that the films are studied over a variety of length scales, and give us the greatest chance to collect all relevant events as a function of time. The two ambient microscopes in our lab are a Nanosurf EasyScan and a Molecular Imaging PicoSPM. The two UHV microscopes are housed in separate chambers. The first is an Omicron Nanotechnology VT-STM XA 50/500 (referred to as the "VT-STM"); this microscope has a temperature range from 28 K to 500 K. The VT-STM chamber also contains a PSP XPS source (Al-K$_\alpha$ and Mg-K$_\alpha$) and analyzer. The second UHV STM we have is an Omicron Nanotechnology LT-STM, which can cool the sample and tip down to 5 K. The superior stability of the UHV STM s will enable us to capture day-long movies of the sample surface for more dilute, less active $^{125}I$.

Preliminary Results

Figure 3A:
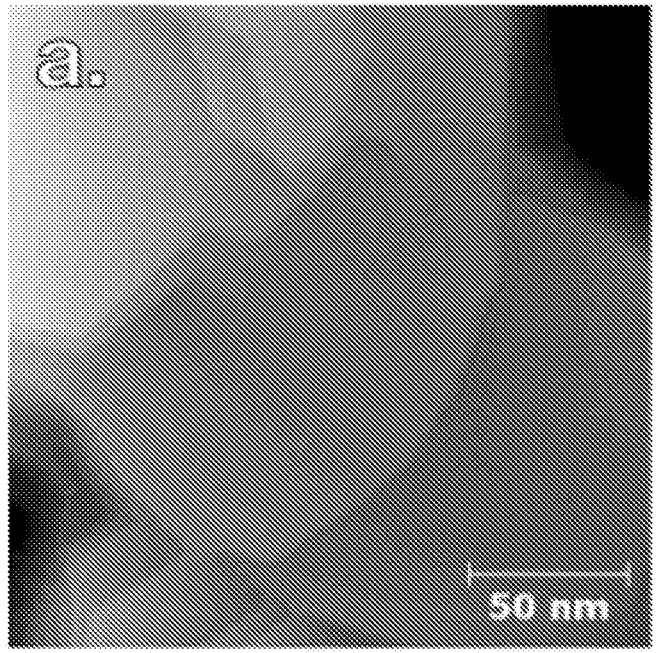
FIG. 3A is an STM image depicting control $^{127}$I-covered Au(111) terraces with very little noise from mobile impurities (V=0.8 V, I=500 pA, image size is 200×200 nm$^2$).
Figure 3B:
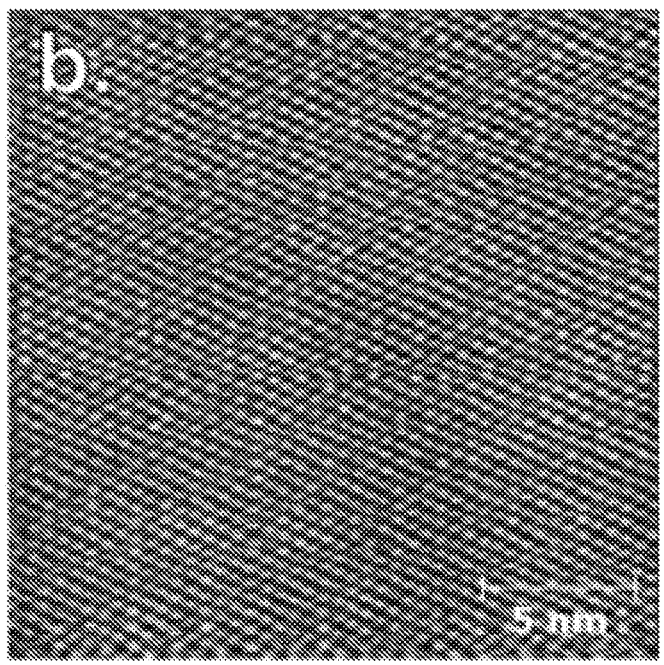
FIG. 3B is an STM image depicting atomic resolution of an iodine monolayer film. Image contains ~2,000 iodine atoms (V=6 mV, I=1 nA, image size is 21×21 nm$^2$).
Figure 4:
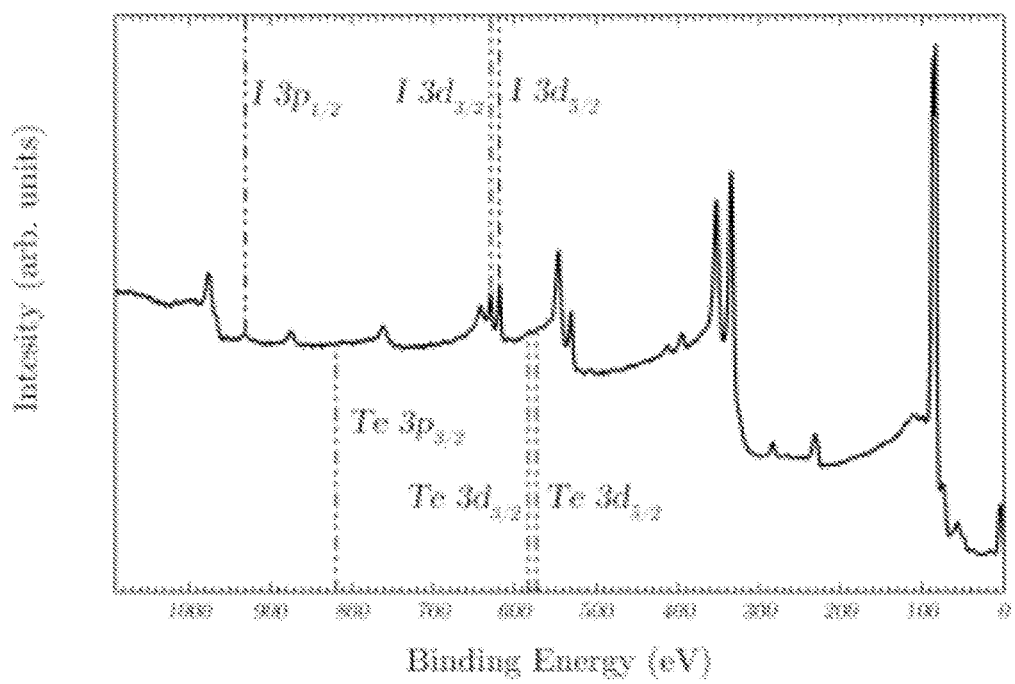
FIG. 4 is a graph depicting an X-ray photoelectron spectra (XPS) survey spectrum of the control $^{127}$I/Au(111) sample. Non-overlapping iodine (I, upper) and tellurium (Te, lower) peaks are denoted with dash-dotted lines. Any reduction in iodine or increase in tellurium content, resulting from the decay of $^{125}$I to $^{125}$Te, will be clearly visible from the respective 3p and 3d core levels.

FIG. 3 shows an $^{127}I$ monolayer scanned in UHV at room temperature. The Au/mica substrate was prepared by $H_2$ flame anneal cleaning in air. The deposition solution for the experiment (0.264 mM NaI and $10^{-5}$ M NaOH, pH 9, in ultra-pure $H_2O$) was made to replicate the solution we will receive from PerkinElmer. The sample was scanned in the VT-STM in UHV after only a simple methanol rinse. The deposition procedure produced large (~100 nm wide) areas of extremely pure $^{127}I$ monolayer film. This level of cleanliness allowed us to acquire atomic resolution over areas large enough to encompass at least 2,000 iodine atoms; larger numbers of atoms will also be included in time-lapse observations of the $^{125}I$ by stitching together multiple images if necessary. The ability to monitor large numbers of atoms in this manner will be pivotal in enabling us to observe, in real time, the decay of individual $^{125}I$ atoms and the spatial distribution of the resultant radiation damage. We will be able to further verify the rate and effects of decay on our samples by tracking the elemental composition in parallel to our imaging measurements. FIG. 4 shows an XPS survey spectrum taken on one of our $^{127}I$ control films where multiple peaks from the iodine can be clearly observed:

$3p_{1/2}$, $3p_{3/2}$, $3d_{3/2}$, and $3d_{5/2}$. If $^{125}$Te (the daughter nuclide) remains on the surface after decay, then there are two 3d core levels, shown in FIG. 4, that will appear at non-overlapping energies with respect to the levels present in the pristine film, making the $^{125}$Te readily apparent as the new element is formed.

Due to the complex stochastic nature of $^{125}$I decay, each decay event is likely to be somewhat unique. As discussed earlier the decay of an $^{125}$I atom has many possible resulting radiation profiles and final daughter states. During STM imaging of the surface we will be able to observe changes in surface adsorption, lateral position, and density of states using STM spectroscopies. The first thing to note is that due to the reduced dimensionality of the surface environment any emission away from the surface will not be observable in STM, nor any of its subsequent consequences. Although this is an obvious point, it is important to note that we will be reducing the amount of damage to the surface by at least half, as compared to a 3-D environment. Our work will uncover the effect of the remaining radiation and how the large amount of backscattered secondary electrons affects the stability of nanostructures.

An interesting question we will be able to answer is the stability of the daughter $^{125}$Te atoms. Previous STM studies have shown that Te can be electro-deposited onto Au(111), and has a well-ordered overlayer structure. Hayden, B E et al. (1997) *J Phys Chem B* 101:7751-7; Sorenson, T A et al. (2001) *Surface Sci* 470:197-214. The major difference in our experiment will be that the daughter $^{125}$Te atoms will be very highly charged. The bond between the highly charged Te and the Au surface atom may destabilize causing desorption; yet we must also consider that the substrate is also a vast well of charge (as it will be grounded during STM/XPS measurement) so it may be possible for the Te to stabilize by acquiring charge. In any case the Te atom will be formed in a position in the iodine monolayer that was ideal for the valency of the parent I atom but not necessarily for the as-formed Te. The under-coordinated tellurium atom will most probably react with the gold surface form telluride ($Te^{2-}$).

The γ- and X-rays emitted from $^{125}$I atoms will not have a significant effect on the local environment because their mean free path is 0.5-20 micrometers (μm), which is much larger than the thickness of the gold film, 150 nm. This is yet another helpful benefit of working at the nanoscale, in that our experimental setup will isolate our window of observation to just the electron emission of the radionuclides, which are believed to be the primary drivers of radiation damage.

During 93% of the $^{125}$Te relaxations the atom will emit a high-energy electron with up to 35 keV of energy (referred to as an "IC-electron"). This electron is part of what is considered primary ionizing radiation in macro-scale reference frames, however, in our experiment IC-electrons will play a somewhat different role. With an energy of 35 keV the inelastic mean free path of an electron in bulk gold is ~24 nm, and when it does interact it should cause the emission of ~40 secondary ionizing electrons per 1 keV of energy lost. We have a good chance of observing the outcome of this interaction during imaging, and we will certainly be able to observe the cumulative effects over large area after a few days. We performed a straightforward Monte Carlo calculation of a surface-bound spherically radiating atom's ability to cause surface irradiation using a uniform angular distribution and an exponentially distributed scattering length. We found that 2.7% of the IC-electron radiation resulted in scattering within the first two Au(111) layers, and that 50% of that was within 1.0 nm of the source atom in the plane of the surface. Although we estimate very few decays to result in surface IC-electron irradiation, we will nonetheless be able to observe their effects with our more enriched films (e.g., the 100% $^{125}$I sample) because we also expect each of these events to have an effect that is highly magnified with respect to the Auger electron emission of a single decay event (1-4 electrons). The Auger electrons which are emitted during the decay process will likely produce a large number of secondary electrons which interact with the film due to inelastic scattering that occurs in the substrate. These electrons will have energies much closer to the strength of chemical bonds and will be the main contributors to film dissociation/damage.

Example 2—Materials and Methods for Example 3

Sample Preparation

Both $^{127}$I (the stable control isotope) and radioactive $^{125}$I films were deposited onto Au(111)/mica substrates from a 161 μM alkaline ($10^{-5}$ M NaOH) solution of NaI in $H_2O$ and dried in air before the excess I was rinsed off with methanol (≥99.9% pure, Sigma-Aldrich). The $^{125}$I films were then transported in air to our lab within 6-33 hours of preparation while being held in a 500 μF capacitor to attenuate surface charge accumulation.

Instrumentation

The parallel plate electron collector experiments took place in an Omicron Nanotechnology LT-STM instrument, with a sample and plate temperature of 80° K to minimize any change in gap size due to thermal fluctuations. The metallic collector plate surface was made by modifying a commercial STM tip holder to be completely flat and then sputter coating it with Au. The graphite collector plate surface was made by affixing a 0.6 mm thick layer of graphite to the collector plate, with the same area. Given the areal density of the (√3×√3)R30° I/Au(111) monolayer, 4.624 atoms/nm$^2$, and the collector plate area, 9.6 mm$^2$ (3.5 mm diameter), the number of atoms sampled is $4.45 \times 10^{13}$. A −9.25% correction was made to this number to account for the age of the sample at the time of measurement (i.e., 9.25% of the originally deposited $^{125}$I had become stable $^{125}$Te), leaving $4.06 \times 10^{13}$ $^{125}$I atoms within the measurement area. Using the differential equation for exponential decay (Equation 1) we calculate that of the $4.06 \times 10^{13}$ $^{125}$I atoms sampled, there will be $5.48 \times 10^6$ decays/s.

$$\frac{dN}{dt} = -\lambda N(t) \qquad (1)$$

With the collector plate at 0.00 V we measure a current of −8.62 pA to the collector and at −10.0 V we measure 3.16 pA; therefore with a −10 V potential in front of the sample surface we are able to supress $7.35 \times 10^7$ electrons/s (|−8.62−3.16 pA|, converted to e−/s). This corresponds to 13.4 e− being emitted from the sample per $^{125}$I decay with less than 10 eV of kinetic energy. Charlton and co-workers calculated that the number of emitted primary electrons with energies <10 eV is 2.1 electrons/decay, only half of which will be emitted away from the sample surface in our experiment. Therefore, the number of secondary electrons emitted from the surface of our sample is 12.4 e−/decay, which is 6 times larger than the calculated value for condensed $^{125}$I.

The other UHV chamber houses a PSP Vacuum Technology X-ray photoelectron spectroscopy system and an Omicron VT-STM XA. Imaging of the stable $^{127}$I/Au films was performed in the VT-STM at room-temperature. The elemental composition change over time due to nuclear decay of the $^{125}$I was tracked with XPS using an Al K$_\alpha$ source. Measurement of the $^{125}$I electron emission was taken using the XPS system's concentric hemispherical electron energy analyser (CHA) (the X-ray source was not used to stimulate emission). Emission spectra were collected with the CHA running in constant retardation ratio (CRR) mode and with the sample at a negative voltage relative to the analyser. Close inspection of FIG. 6 reveals the initial Te formed in the 4+ oxidation state caused by exposure to air during transportation of the as formed sample.

DFT Results

Density functional theory (DFT) calculations with the Perdew-Burke-Ernzerhof (PBE) exchange-correlation functional were performed as part of this study. The periodic plane wave DFT code VASP was used. Valence electrons were expanded in plane waves with a cut-off energy of 300 eV, while core electrons were replaced by projector augmented wave (PAW) potentials. The unreconstructed Au(111) surface was modelled by a 4 atomic layer thick slab with a variety of lateral unit cells, so as to model different adsorption structures at different I and Te coverages. The Au atoms in the bottom layers were fixed at their bulk-truncated positions and the PBE lattice constant was used throughout. A 15 Å vacuum along the surface normal was used to separate slabs in adjacent cells. A 6×6×1 Monkhorst-Pack k-point grid was used per √3×√3 unit cell for the structure optimizations. The wavefunction was re-computed from the optimized structures with a 14×14×1 Monkhorst-Pack k-point grid per √3×√3 unit cell for the STM simulations. The Tersoff-Hamann approximation with an s-like tip was used to simulate the STM images. The pure I monolayer and the mixed Te/I monolayer were modeled at a coverage of ⅓ of a monolayer, which corresponds to four adsorbate atoms per 2√3×2√3 unit cell, four I atoms in the case of the pure I monolayer, and three I and one Te atom for the mixed monolayer.

Adsorption energies E$_{ads}$ were computed with Equation 2, $$E_{ads} = E_{AuI3/X} - E_{AuI3} - E_X \quad (2)$$

where E$_{AuI3/X}$ is the total energy of the adsorbed monolayer (either a pure iodine or a mixed iodine/tellurium monolayer) on Au, E$_{AuI3}$ the energy of an I overlayer with one unoccupied adsorption site on the gold surface, and E$_X$ the energy of the an isolated X (X=I, Te) atom in the gas phase. The most stable adsorption site for Te and I was found to be the hollow site for both species. The adsorption energy according to Equation 2 was found to be −3.1 eV and −2.1 eV for Te and I respectively. Thus Te interacts more strongly with the Au(111) surface than I does.

Electron Scattering Inside of a Spherical Substrate

The key parameter that makes Au films analogous to nanoparticles is the short inelastic mean free path (IMFP) of the electron in Au metal (0.4-24 nm in the 10-35,000 eV energy range, as shown in Table 2). We note that 80% of the total primary radiation from $^{125}$I has an IMFP less than 1 nm—well below the typical nanoparticle diameter. The particle size effect can be quantified by integrating the proportion of electrons that undergo their first scattering event within the nanoparticle's spherical volume over all angles of emission.

$$N_{tot} = \frac{1}{2}\sum_\varepsilon \left[ N_\varepsilon \int_0^{\frac{\pi}{2}} \left(1 - e^{-\frac{D}{\beta_\varepsilon}\cos\theta}\right) \sin\theta \, d\theta \right] \quad (3)$$

-continued $$= \frac{1}{2}\sum_\varepsilon \left[ N_\varepsilon \left( \frac{\beta_\varepsilon}{D}\left(e^{-\frac{D}{\beta_\varepsilon}} - 1\right) + 1 \right) \right]$$

Equation 3 shows this integral and its result after evaluation, where ε is the kinetic energy of the emitted electrons, N$_\varepsilon$ are their yields (per decay), β$_\varepsilon$ are their mean free paths in Au, and D is the diameter of the particle. Table 3 shows the results as a function of nanoparticle diameter, noting that 5.6 e$^-$ are scattered per decay in the planar Au substrate. It is known that 10 nm nanoparticles or smaller are able to penetrate the cell nucleus; from our calculations nanoparticles of this size would only have a 14% reduction in electrons that would undergo at least one inelastic scattering event. Furthermore, previous Monte Carlo studies have shown that the emitted secondaries from a primary electron of 250 eV incident upon Al will all be generated within 2 nm of the surface. Given that 80% of $^{125}$I primaries in Au are of similar or shorter IMFP to a 250 eV electron in Al, we assert that a 10 nm particle would be large enough to accommodate the full cascade of scattering events that produce the secondary electron cascade.

TABLE 2

Electron inelastic mean free path in Au for relevant kinetic energies.

| Kinetic Energy (eV) | IMFP (nm) |
| --- | --- |
| 20 | 1.0 |
| 30 | 0.7 |
| 90 | 0.4 |
| 200 | 0.5 |
| 300 | 0.6 |
| 500 | 0.8 |
| 3,000 | 3.1 |
| 35,000 | 23.8 |

TABLE 3

Nanoparticle scattering. Reduction is relative to planar Au substrate

| Particle diameter (nm) | Electrons scattered (cnt/decay) | Reduction |
| --- | --- | --- |
| 5 | 4.3 | 24% |
| 10 | 4.8 | 14% |
| 15 | 5 | 10% |
| 20 | 5.2 | 7.90% |
| 30 | 5.3 | 5.50% |
| 50 | 5.4 | 3.50% |
| 100 | 5.5 | 1.80% |
| 200 | 5.6 | 0.89% |

Example 3

This example describes a straightforward method for synthesizing monolayer films of radioactive $^{125}$I atoms on gold-coated mica substrates under ambient conditions, and characterizing their composition and their electron emission. Despite being synthesized from radioactive $^{125}$I (>99.9% purity), they are robust with respect to self-destruction, and provide well-defined, intense planar sources of secondary electrons. $^{125}$I decays by electron capture (EC) of a core shell electron to produce a nuclear excited state of $^{125}$Te, the majority of which eject another core shell electron during de-excitation. A cascade of electronic relaxations following the creation of each core hole leads to emission of multiple electrons. Most of these emitted electrons have >10 eV kinetic energy and their distribution in energy is very sensitive to the local chemical environment. This rapid electron emission (within ~1 ns) leaves the daughter $^{125}$Te atom in a highly charged state (up to Te$^{25+}$), and in a condensed material or molecule the sudden charging makes the system susceptible to fragmentation (via Coulomb explosion) without sufficiently fast neutralization. Therefore, a major challenge in realizing a nano-structured radiation source is the design of a system that is robust under the ultra-fast release of energy and particles that accompany each atomic decay event. In anticipation of this challenge we have chosen $^{125}$I/Au for this work, because the well-known, robust I/Au chemistry makes this system a good candidate for a stable 2-D emitter.

Figure 5:
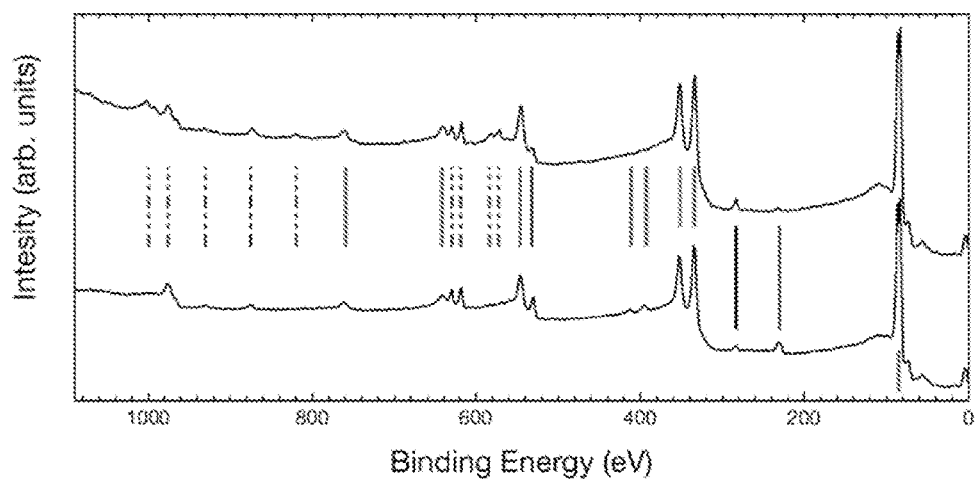
FIG. 5 depicts survey XPS taken after preparation and transportation, demonstrating no major contamination of $^{125}$I samples during deposition or exposure to ambient conditions.

Samples were prepared using an ambient drop-casting method adapted from the previous (non-radioactive) $^{127}$I/Au work of Huang et al., *J Chem Phys* 107: 585 (1997). Survey X-ray photoelectron spectra (XPS) taken after preparation and transportation indicated no major contamination of the $^{125}$I samples during deposition or exposure to ambient conditions (FIG. 5).

Figure 6:
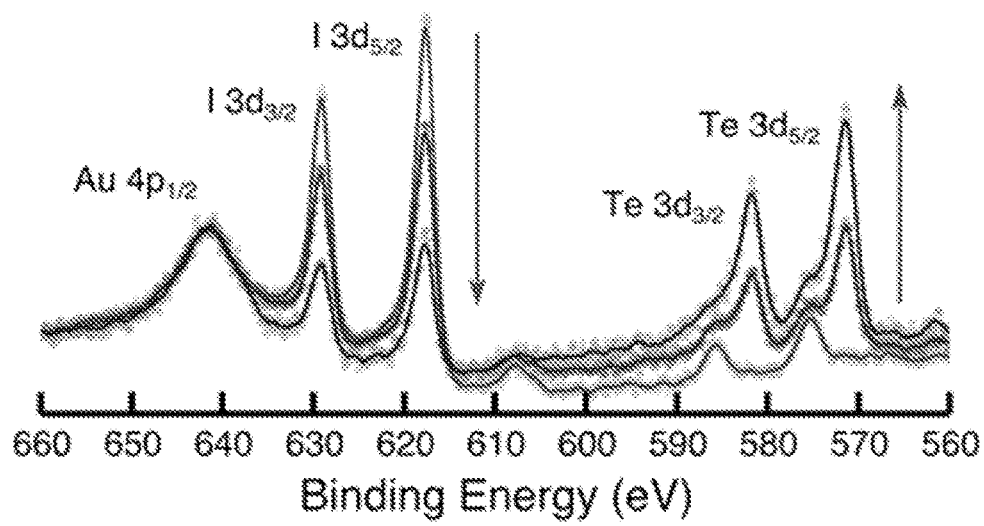
FIG. 6 depicts XPS of radioactive $^{125}$I film as a function of time, showing the nuclear transmutation of $^{125}$I into $^{125}$Te, and the daughter $^{125}$Te atom remains bound to the surface. Elemental core levels are labeled, and arrows highlight the change of I to Te over time.

In order to track the nuclear transmutation of $^{125}$I to $^{125}$Te, XPS measurements of the sample were taken as a function of time. By measuring the I and Te 3d core levels with XPS we directly observed the nuclear transmutation of $^{125}$I to $^{125}$Te as a decrease in the I and an increase in the Te signals over time (FIG. 6). The sample never left vacuum over the course of the XPS measurements and hence the newly formed $^{125}$Te atoms appear in the spectrum with a binding energy of 582 (3d$_{3/2}$) and 572 (3d$_{5/2}$) eV, as expected for the Te$^0$ oxidation state. These XPS measurements clearly showed that the films withstand ambient processing (based on initial XPS surveys after synthesis and transportation), and that the newly formed $^{125}$Te daughter was resistant to desorption.

Film structure was imaged with scanning tunnelling microscopy (STM) to search for atomic-scale damage near the $^{125}$Te species observed in XPS. Theoretical studies have indicated that the decay of condensed phase $^{125}$I leads to an average total energy of 18.3 keV being deposited into its surroundings in the form of hot electrons. When using the traditional convention of only considering total deposited energy, it would be reasonable to suspect film damage via local atomic desorption in $^{125}$I films. However this is not what we observed; when imaging 100×100 nm$^2$ areas or larger (FIG. 7a), no damage was visible, and the $^{125}$I films appeared identical to those of stable $^{127}$I control films. High-resolution imaging of smaller areas (FIG. 7a, inset; and FIG. 7b) yields atomic resolution of the $^{125}$I monolayer in the expected (√3×√3)R30° structure. In total, imaging of the radioactive monolayer structure at many scales showed that the $^{125}$I film was not damaged by self-irradiation. We observed the appearance of atom-sized depressions randomly distributed throughout the $^{125}$I monolayer which are not present in the $^{127}$I control films which we assigned as $^{125}$Te atoms resulting from the nuclear transmutation of $^{125}$I.

Figure 8:
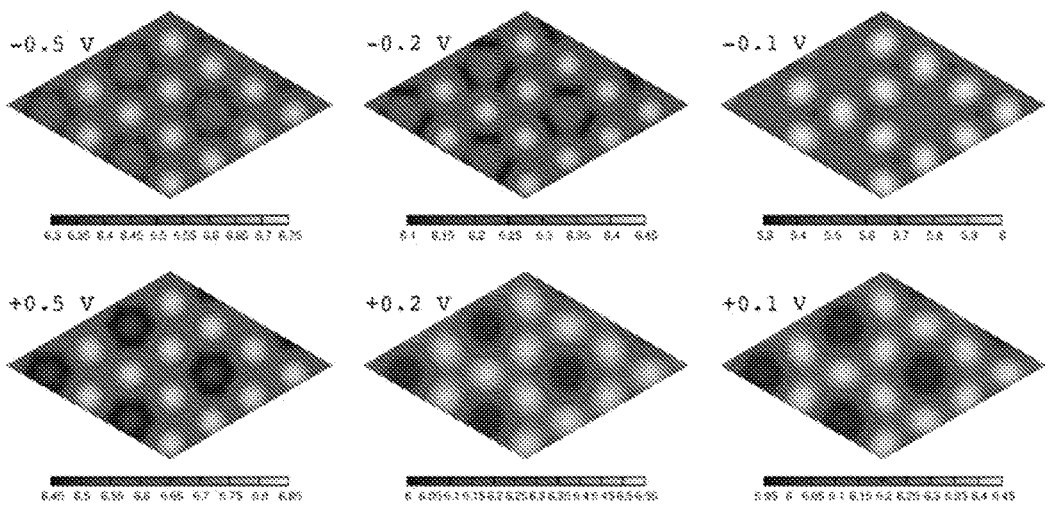
FIG. 8 depicts simulated STM of the Te/I monolayer with a smaller tip-sample distance. The z-axis corresponds to the tip height relative to the Te/I monolayer at which the LDOS has a value of $10^{-9}$ e/Å$^3$. The bright spots correspond to I atoms, the darker ones to Te atoms.
Figure 9:
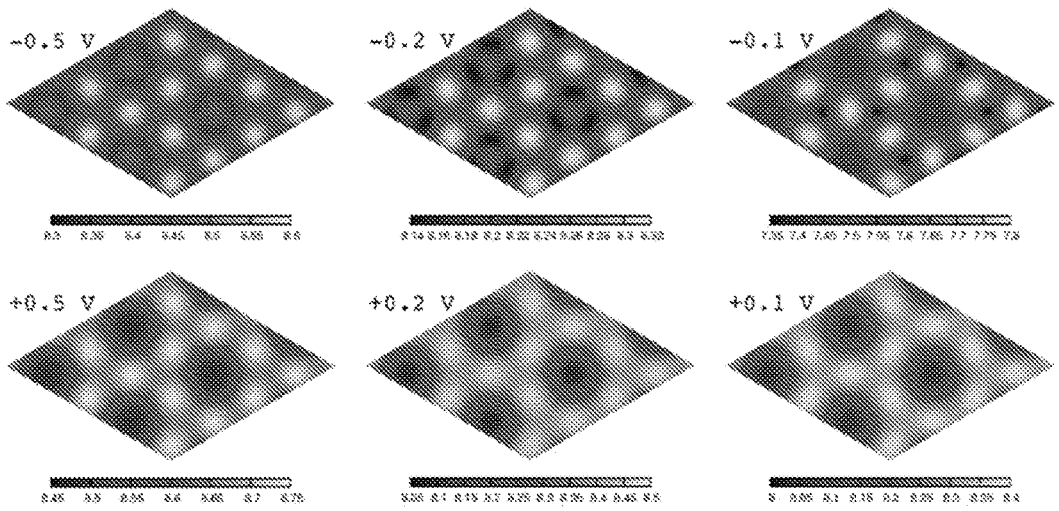
FIG. 9 depicts simulated STM of the Te/I monolayer with a larger tip-sample distance. The z-axis correspond to the tip height relative to the Te/I monolayer at which the LDOS has a value of $10^{-11}$ e/Å$^3$. The bright spots correspond to I atoms, the darker ones to Te atoms.

The striking resilience of the radioactive film can be explained by the density functional theory calculations (DFT) we performed for various I, Te, and mixed I/Te overlayers. We determined the most stable adsorption sites for both I and Te as the three-fold hollow sites by placing the adsorbates at a variety of high-symmetry adsorption sites. The simulated STM imaging for this overlayer structure (illustrated in FIG. 7c) indicate that the Te atoms do indeed appear as depressions with respect to the I atoms (See FIGS. 8 and 9 where it is shown that this is the case for all biases considered). This difference in apparent height is primarily due to the Te atoms being bound more strongly to the Au(111) surface and subsequently having a shorter bond length (268 pm for Te, 291 pm for I).

Figure 7:
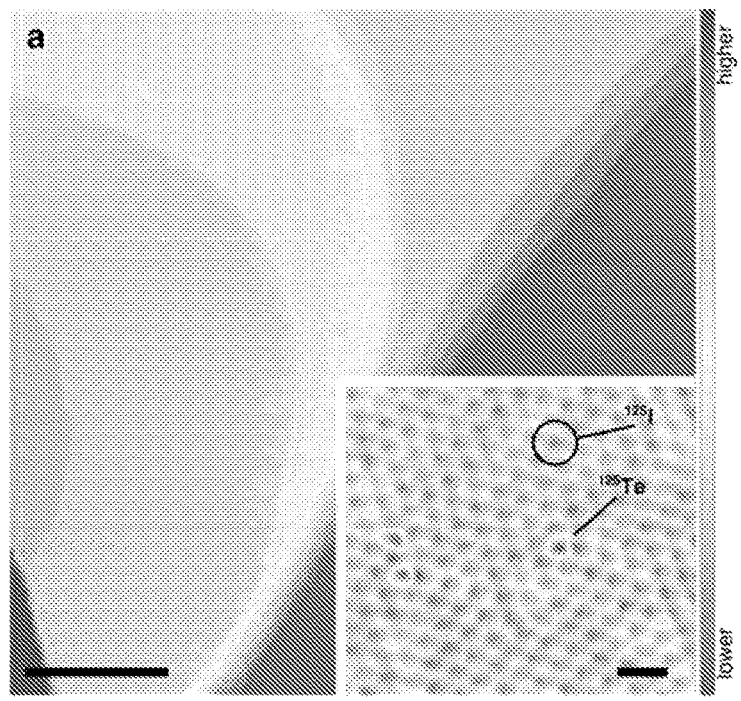
FIG. 7a depicts STM images of $^{125}$I films, demonstrating flat I-covered Au terraces separated by atomic steps (main image: V=+100 mV, I=1 nA and 50 nm scale bar) and atomic resolution of $^{125}$I atoms in ($\sqrt{3}\times\sqrt{3}$)R30° overlayer (inset: V=−400 mV, I=100 pA and 1 nm scale bar).
FIG. 7b is a high resolution STM image depicting a $^{125}$Te atom feature topographically lower than the neighboring I atoms (V=100 mV, I=10 pA).
FIG. 7c depicts repeating density functional theory (DFT) structure (top; I in darker shade and Te in lighter shade) and DFT-based simulated STM image (bottom) indicate that these features are isolated Te atoms which appear topographically lower than their I neighbors due to the shorter, stronger Te—Au bond.
FIG. 7d is a schematic representation of stochastic nuclear transmutation of individual atoms in the monolayer geometry ($^{125}$I in darker shade, $^{125}$Te in lighter shade).
Figure 7:
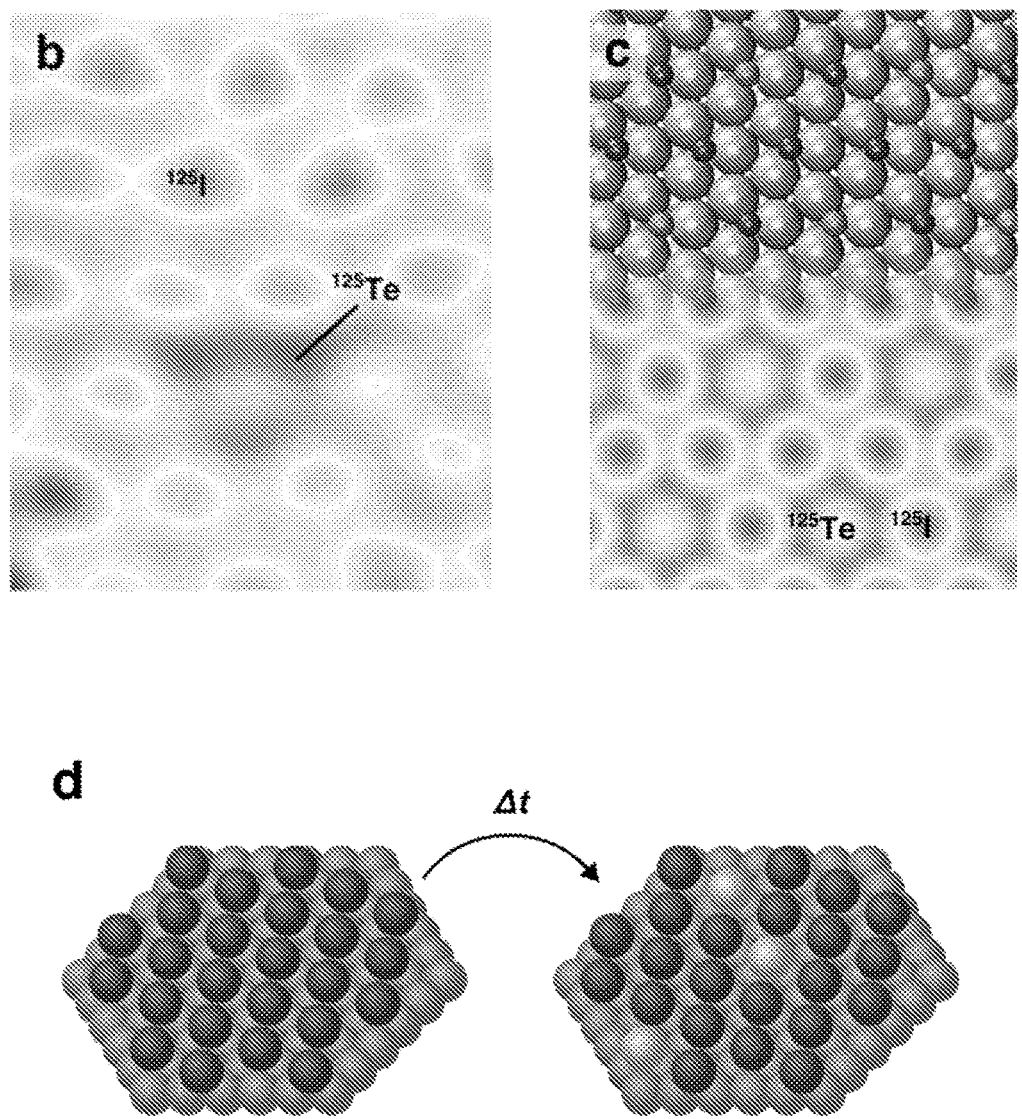

Experimental images with STM tip states that provide very high spatial resolution revealed a central protrusion within the depressions corresponding to the Te atom, which is consistent with our DFT-simulated STM images (FIG. 7b, c). Furthermore, the results of the DFT calculations explained the experimentally observed film stability. The calculated I—Au and Te—Au binding energies, 2.1 eV and 3.1 eV, respectively, are much larger than the nuclear recoil energy (<0.1 eV), thus preventing rupture of the surface bonds following decay. Importantly, there is also substantial hybridization of the I/Te valence orbitals with the Au surface which we postulate imparts resilience against Coulomb explosion by allowing fast electron transfer from the Au surface that rapidly neutralizes the atom undergoing decay.

Figure 10A:
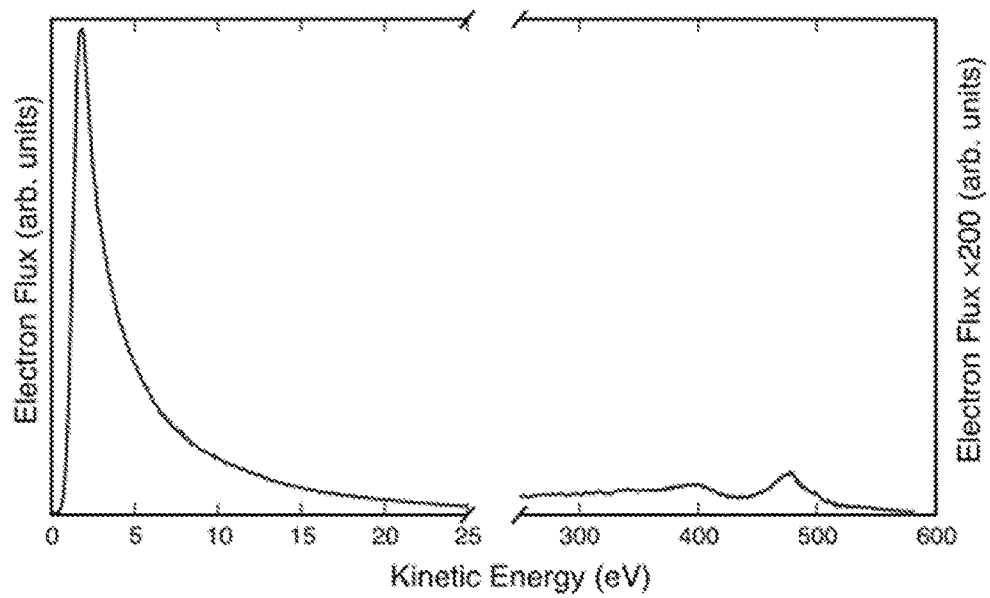
FIG. 10a is a graph depicting electron emission spectrum from radioactive $^{125}$I monolayer. Representative electron emission spectrum shows that, in addition to the expected electron capture decay process Auger peaks at 480 eV (intensity×200), a multitude of low-energy (0-20 eV) electrons are emitted from the $^{125}$I/Au film.

In order to probe the performance of the $^{125}$I/Au films as low-energy electron emitters, electron emission spectra were recorded in the 0-600 eV kinetic energy range with a 5-channel concentric hemispherical electron energy analyser. The emission spectrum (FIG. 10a) showed the electron energy distribution was concentrated in the desired region of 0-20 eV and a smaller peak at 480 eV that arises from Auger transitions in the daughter $^{125}$Te atom during the core hole relaxation cascade. To quantify the number of emitted electrons we brought a flat Au-coated plate (3.5 mm diameter) within 0.1 mm of the grounded sample surface in vacuum and recorded the electrical current. By applying a negative potential to the collector plate it was possible to suppress, and hence quantify, the low-energy electron flux flowing from the radioactive sample to the collector. Application of −10 V to the collector plate suppressed the electron flow by 11.8 pA. The half-life of $^{125}$I, the age of the sample (8 days), and the density of $^{125}$I atoms in the monolayer were known, and we calculated that there are 13.4 electrons emitted per $^{125}$I decay with a kinetic energy <10 eV.

Figure 10B:
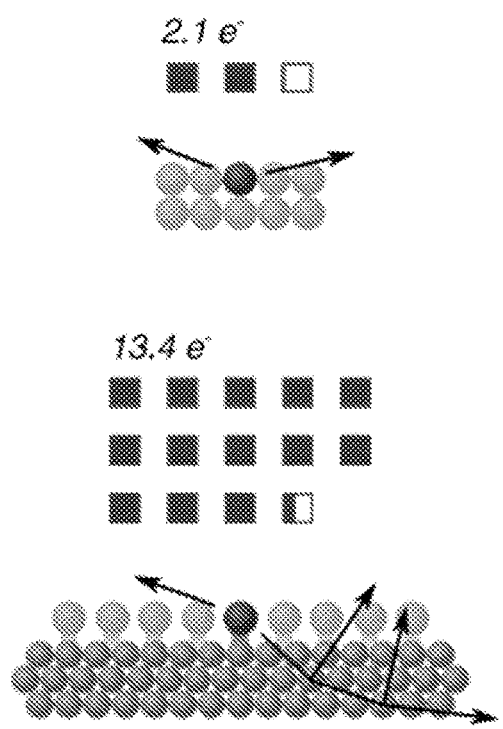
FIG. 10b is a cartoon depicting schematic representation of electron backscattering from the metal film (lower panel) which leads to six-fold enhancement of low-energy electron emission compared to condensed phase $^{125}$I (upper panel). Each box represents the average emission of 1 electron per decay with kinetic energy <10 eV.

The 2-D interface geometry of our radiation source dictates that half of the primary electrons emitted from decaying $^{125}$I atoms are directed into the metal substrate, and those with higher energies should be expected to backscatter lower energy secondary electrons, in an analogous manner to secondaries generated during electron spectroscopy and diffraction experiments. An interesting effect occurs when the collector is biased at −10 V; the net current flow reverses compared to when the sample and collector are unbiased, and (at −10 V) electrons flow from the collector to the sample. This is because the high energy primaries from the radioactive sample generate secondary electrons in the collector plate that dominate the electrical current when the secondary electrons from the sample are suppressed. Although we expect some enhancement of the low-energy primary electron emission due to hybridization between the $^{125}$I atoms and the Au surface, this experiment demonstrates the significance of the secondary emission from Au metal induced by primary emission of the radioactive decay. Our $^{125}$I films emit a low-energy (0-10 eV) electron flux that is >600% that of condensed $^{125}$I when deposited on Au(111) (FIG. 10b) mainly via inelastic scattering, which will be a universal behavior for metal substrates.

The influence of the substrate material can be examined using this setup. We found a ~20% reduction in the secondary emission induced by the $^{125}$I monolayer in a ~0.6 mm thick disc of graphite attached to the collector, which illustrates the benefits of a metal substrate in amplifying the yield of chemically-active low-energy electrons.

In summary, we report a method for making air-stable, planar and atomically well-defined radiation sources that emit high fluxes of low-energy electrons. This system has enabled us to image nuclear transmutation with atomic-scale resolution. Looking forward, the simplicity of this approach for making 2-D radioactive films, coupled with the abundance of established experimental procedures for nanopatterning substrates and functionalizing nanoparticles will open up many new possibilities. For example, electron transmission through thin films of water, proteins, and DNA adsorbed on well-defined radioactive substrates would help quantify the local effect of secondary electrons; this would provide a microscopic understanding of radiation chemistry, biological degradation, and material damage. Moreover, the I—Au surface chemistry used in our model system is compatible with functionalized Au nanoparticles, which are commonly used in many aspects of biology and medicine to target specific sites within cells.

Given that 80% of the primary electrons ejected from $^{125}$I have an inelastic mean free path less than 2 nm, $^{125}$I-coated nanoparticles are expected to also generate high fluxes of low-energy electrons. The prospects for $^{125}$I/Au nanoparticle stability in a biological environment are promising as it is well known that iodine-coated Au nanoparticles are very stable in solution due to strong I—Au bonds, and our DFT calculations reveal that the Te—Au bond is even stronger. The 600% amplification in low-energy electron emission of the radioactive $^{125}$I/Au system described here highlights the potential for targeted radio-iodine coated Au nanoparticles that increase their efficacy per nuclear decay while minimizing bystander damage due to the short mean free path of the emitted low-energy electrons.

INCORPORATION BY REFERENCE

All patents and published patent applications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

We claim:

1. A composition, comprising: a substrate; and a film enriched with a radioisotope relative to the natural abundance of said radioisotope; wherein said substrate comprises an outside surface; the outside surface is in contact with the film; the film has a thickness of one to ten atomic or molecular layers; the radioisotope is $^{125}$I; and the outside surface comprises gold.

2. A composition, comprising: a substrate; a film enriched with a radioisotope relative to the natural abundance of said radioisotope; and an intervening layer; wherein said substrate comprises an outside surface; said intervening layer is positioned between the outside surface of the substrate and the film; the intervening layer comprises an inner surface and an outer surface; said outside surface is in contact with said inner surface; said outer surface is in contact with said film; the film has a thickness of one to ten atomic or molecular layers; the radioisotope is $^{125}$I; and the outer surface comprises gold.

3. A method of making the composition of claim 1, comprising:
    contacting a source of the radioisotope with the outside surface of the substrate, wherein the source of the radioisotope is enriched with the radioisotope relative to the natural abundance of said radioisotope; the radioisotope is $^{125}$I; and the outside surface comprises gold.

4. A method of making the composition of claim 2, comprising:
    contacting a source of the radioisotope with the outer surface of the intervening layer, wherein the source of the radioisotope is enriched with the radioisotope relative to the natural abundance of said radioisotope; the radioisotope is $^{12}$I; and the outer surface comprises gold.

5. A microarray or nanoarray, comprising the composition of claim 1, wherein the film is patterned.

6. A power source, comprising the composition of claim 1.

7. A sensing device, comprising the composition of claim 1.

8. An implantable medical device, comprising the composition of claim 1.

9. A method of delivering low-energy electrons to a liquid, solid, molecular layer, or cell, comprising contacting a liquid, solid, molecular layer, or cell with the composition claim 1.

10. A microarray or nanoarray, comprising the composition of claim 2, wherein the film is patterned.

11. A power source, comprising the composition of claim 2.

12. A sensing device, comprising the composition of claim 2.

13. An implantable medical device, comprising the composition of claim 2.

14. A method of delivering low-energy electrons to a liquid, solid, molecular layer, or cell, comprising contacting a liquid, solid, molecular layer, or cell with the composition of claim 2.

15. The composition of claim 1, wherein the outside surface is gold.

16. The composition of claim 1, wherein the substrate is gold.

17. The composition of claim 1, wherein the substrate is a gold nanoparticle.

18. The composition of claim 2, wherein the outer surface is silver.

19. The composition of claim 2, wherein the intervening layer is gold.

20. The composition of claim 19, wherein the substrate is a nanoparticle.

21. The method of claim 9, wherein the composition of claim 15 is used.

22. The method of claim 9, wherein the composition of claim 16 is used.

23. The method of claim 9, wherein the composition of claim 17 is used.

24. The method of claim 14, wherein the composition of claim 18 is used.

25. The method of claim 14, wherein the composition of claim 19 is used.

26. The method of claim 14, wherein the composition of claim 20 is used.

* * * * *